United States Patent [19]

Panzer et al.

[11] 4,127,719
[45] Nov. 28, 1978

[54] METHOD OF PREPARING PYRIMIDINES

[75] Inventors: Hans P. Panzer, Stamford; Michael N. D. O'Connor, Norwalk; Louis J. Baccei, Newington, all of Conn.

[73] Assignee: American Cyanamid Company, Stamford, Conn.

[21] Appl. No.: 774,307

[22] Filed: Mar. 4, 1977

Related U.S. Application Data

[62] Division of Ser. No. 706,084, Jul. 16, 1976, Pat. No. 4,039,542, which is a division of Ser. No. 467,331, May 6, 1974, Pat. No. 4,006,247.

[51] Int. Cl.$^2$ ............................................. C07D 239/06
[52] U.S. Cl. .................................................... 544/242
[58] Field of Search ................................ 548/335, 347; 260/251 R, 699 QZ, 682; 544/242

[56]  References Cited
      U.S. PATENT DOCUMENTS

| 2,427,337 | 9/1947 | Abbott et al. | 260/699 QZ |
|---|---|---|---|
| 2,478,270 | 8/1949 | Ipatieff et al. | 260/682 |
| 2,537,638 | 1/1951 | Kitchen | 260/699 QZ |
| 2,588,123 | 3/1952 | Kern | 260/699 QZ |
| 2,591,587 | 4/1952 | Mowry | 260/699 QZ |
| 2,634,302 | 4/1953 | Seymour et al. | 260/699 QZ |
| 3,375,289 | 3/1968 | Khchejan et al. | 260/699 QZ |
| 3,523,123 | 8/1970 | Wehrmeister | 548/347 |
| 3,526,674 | 9/1970 | Becker et al. | 260/669 QZ |
| 3,658,928 | 4/1972 | Skinner et al. | 260/669 QZ |

OTHER PUBLICATIONS

Fieser et al. Organic Chemistry 3rd Ed. pp. 53–57, N.Y., Reinhold, 1956.
Somerset et al. Chem. Abst. 1972, vol. 77, No. 152187u.
Wehrmeister Chem. Abst. 1965, vol. 63, Column 610.

Primary Examiner—Natalie Trousof
Attorney, Agent, or Firm—Frank M. Van Riet

[57]  ABSTRACT

Compounds having the formula

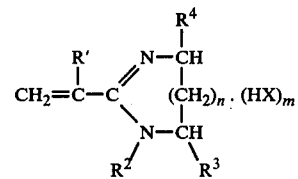

wherein $n$ and $m$ are, individually, 0 or 1, X is an anion, R' is hydrogen, methyl or phenyl and $R^2$, $R^3$ and $R^4$ are, individually, hydrogen, alkyl, aryl, alkaryl or aralkyl, polymers thereof and methods for their production, are disclosed.

12 Claims, No Drawings

METHOD OF PREPARING PYRIMIDINES

This is a division of application Ser. No. 706,084, filed July 16, 1976, now U.S. Pat. No. 4,039,542 which, in turn, is a division of application Ser. No. 467,331, filed May 6, 1974 and now U.S. Pat. No. 4,006,247.

BACKGROUND OF THE INVENTION

The use of high-efficiency products in the treatment of aqueous suspensions of particulate, solid, water-insoluble materials has become increasingly prevalent in recent years. Industry, in general, and research, in particular, are therefore continually searching for new systems which can be employed to facilitate the dewatering of aqueous suspensions of organic, or mixtures of organic and inorganic, materials such as distillary wastes, fermentation wastes, wastes from paper manufacturing plants, dye plant wastes and sewage suspensions such as digested sludges, activated sludges or raw and primary sludges from sewage treatment plants, etc.

The most recent and most successful materials introduced for the treatment of such suspensions have been the amidine and imidazoline polymers, see U.S. Pat. Nos. 3,406,139; 3,450,646; 3,576,740; 3,666,705, hereby incorporated herein by reference. These polymers are very effective materials for use in the treatment of industrial wastes. The polymers, however, are produced by the treatment of corresponding nitrile polymers and their structures are therefore governed by the structure of the nitrile polymer from which they are made. Furthermore, conversion of the nitrile polymers to the imidazoline or amidine polymers does not reach 100% and a portion of the resultant polymer is, therefore, non-functional in its water treating capacity.

Prior attempts to obviate these difficulties have included rearrangement of the groups present in the nitrile polymer charge and the attempted production of unsaturated imidazolines which may be homopolymerized or copolymerized into more active imidazoline polymers. Attempts to produce intermediates from which the unsaturated imidazolines may be prepared have, however, proven unsuccessful. Additionally, attempts to follow the teachings of U.S. Pat. No. 3,210,371 resulted only in the production of polymers while the teachings of Oxley et al, Jour. Chem. Soc., 1947, pgs. 497–505 also resulted in the recovery of polymeric products.

SUMMARY

We have now succeeded in the production of a novel class of monomers which can be polymerized into polymers useful in the treatment of water sludges, the formation of fibers and the treatment of paper.

DESCRIPTION OF THE INVENTION INCLUDING PREFERRED EMBODIMENTS

The novel compounds of the present invention have the formula

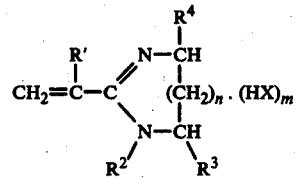

where $n$ and $m$ are, individually, 0 or 1, X is an anion, i.e., a negative salt forming ion or radical, R' is hydrogen, methyl or phenyl and $R^2$, $R^3$ and $R^4$ are, individually, hydrogen, alkyl ($C_1$–$C_4$), aryl ($C_6$–$C_{10}$), alkaryl ($C_7$–$C_{11}$) or aralkyl ($C_7$–$C_{11}$).

The compounds of Formula (I), wherein $m$ is 0, are prepared by heating to a cracking temperature of from about 275° C. to about 500° C., in the absence of acids or salts, a compound having the formula

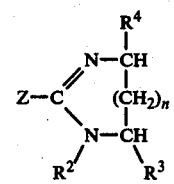

wherein Z is

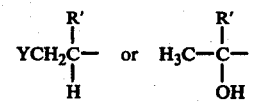

wherein Y is hydroxyl or RO, R being alkyl ($C_1$–$C_{10}$), aryl ($C_6$–$C_{10}$) or aralkyl ($C_7$–$C_{11}$) and $n$, R', $R^2$, $R^3$ and $R^4$ are as set forth above. The compounds of Formula (II) are disclosed and claimed in our copending application, Ser. No. (Case No. 25,210), filed concurrently herewith and entitled COMPOUNDS now U.S. Pat. No. 4,007,200, which application is hereby incorporated herein by reference.

These novel compounds ($m=0$) are preferably prepared at subatmospheric pressure although atmospheric or superatmospheric pressures may be used under certain variable conditions, if necessary or desired.

The production of these compounds ($m=0$) proceeds according to the equation:

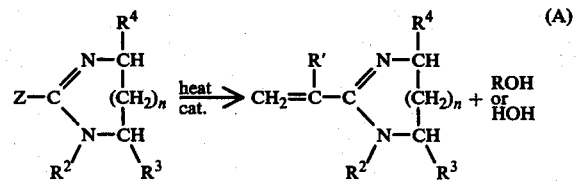

wherein all variables are as described above.

The charge material of Formula (II) is preferably melted and converted into a gas before it is heated to the above described cracking temperature and passed through an appropriate catalyst. Catalysts which have been found to be useful for this purpose can generally be described as heterogenous vapor phase catalysts. More particularly, they may be described as inorganic oxide gels, alkaline earth metal oxides and mixtures thereof. Examples of materials which have been found to be useful as catalysts herein include barium oxide, alumina, silica gel, thorium oxide on silica gel, calcium oxide on silica gel, barium oxide on silica gel, barium oxide on alumina and the like. Other related catalysts known to those skilled in the art can also be used.

The product produced according to the above method is usually formed as an an admixture with other by-product materials, the desired product being recoverable by distillation, extraction, crystallization and the like.

In a preferred embodiment, we have found that the presence of small amounts of water, i.e. up to about 30%, by weight, based on the total feed or charge compound weight, materially enhances the yield of the vinyl ($m=0$) compound recovered. That is to say, when the charge compound of Formula (II) contains the above amount of water, preferably from about 2.0% to about 30.0%, the yield of Formula (I), $m=0$, product is materially enhanced.

When the unsaturated compounds produced according to Equation A, above, are contacted, usually under ambient conditions, with an acid, e.g. sulfuric, hydrochloric, nitric, acetic, malonic, tartaric, benzoic etc., the compounds of Formula I, wherein $m$ is 1 are formed. These compound salts are preferably produced by merely collecting the effluent from the cracking operation in the appropriate acid, although the vinyl compound may be recovered per se and converted to the salt subsequently, if desired. It is preferred to convert the vinyl compounds into their corresponding salts since the salts are more stable than the vinyl compounds per se.

As mentioned above, all the vinyl compounds of Formula (I), above, find use in the preparation of homopolymers and copolymers thereof. The compounds homopolymerize at elevated temperatures spontaneously or they may be homopolymerized at lower temperatures utilizing free radical catalysts, for example, benzoyl peroxide, azobisisobutyronitrile etc. All the vinyl compounds of Formula (I) may be copolymerized with one, two or any desired number of comonomers, the particular number involved depending on the particular service application to which the copolymers are to be put. When comonomers are used, they may be employed in amounts ranging from about 4% to 96%, by weight, based on the total monomer charge, the preferred amount being about 25-75%. Examples of useful comonomers which may be copolymerized, preferably under normal vinyl polymerization conditions, include the unsaturated alcohol esters, more particularly the allyl, methallyl, crotyl, 1-chloroallyl, 2-chloroallyl, cinnamyl, vinyl, methvinyl, 1-phenylallyl, butenyl, etc., esters of saturated and unsaturated aliphatic and aromatic monobasic and polybasic acids such, for instance, as acetic, propionic, butyric, valeric, caproic, crotonic, oxalic, malonic, succinic, glutaric, adipic, pimelic, suberic, azelaic, sebacic, maleic, fumaric, citraconic, mesaconic, itaconic, acetylene dicarboxylic, aconitic, benzoic, phenylacetic, phthalic, terephthalic, benzoylphthalic, etc., acids; the saturated monohydric alcohol esters, e.g., the methyl, ethyl, propyl, isopropyl, butyl, sec.-butyl, amyl, etc., esters of ethylenically unsaturated aliphatic monobasic and polybasic acids, illustrative examples of which appear above; vinyl cyclic compounds (including monovinyl aromatic hydrocarbons), e.g., styrene, o-, m-, and p-chlorostyrenes, -bromostyrenes, -fluorostyrenes, -methylstyrenes, -ethylstyrenes, -cyanostyrenes, the various poly-substituted styrenes such, for example, as the various di-, tri-, and tetrachlorostyrenes, -bromostyrenes, -fluorostyrenes, -methylstyrenes, -ethylstyrenes, -cyanostyrenes, etc., vinyl naphthalene, vinylcyclohexane, vinyl furane, vinyl pyridine, vinyl dibenzofuran, divinyl benzene, trivinyl benzene, allyl benzene, diallyl benzene, N-vinyl carbazole, the various allyl cyanostyrenes, the various alpha-substituted styrenes and $\alpha$-substituted ringsubstituted styrenes, e.g., $\alpha$-methyl styrene, $\alpha$-methyl-paramethyl styrene, etc.; unsaturated ethers, e.g., ethyl vinyl ether, diallyl ether, ethyl methallyl ether, etc.; unsaturated amides, for instance, N-allyl caprolactam, acrylamide, and N-substituted acrylamides, e.g., N-methylol acrylamide, N-allyl acrylamide, N-methyl acrylamide, N-phenyl acrylamide, etc.; unsaturated ketones, e.g., methyl vinyl ketone, methyl allyl ketone, etc.; methylene malonic esters, e.g., methylene methyl malonate, etc.; ethylene; unsaturated polyhydric alcohol (e.g., butenediol, etc.) esters of saturated and unsaturated, aliphatic and aromatic, monobasic and polybasic acids.

Other examples of monomers that can be copolymerized with the monomers of Formula I are the vinyl halides, more particularly vinyl fluoride, vinyl chloride, vinyl bromide and vinyl iodide, and the various vinylidene compounds, including the vinylidene halides, e.g., vinylidene chloride, vinylidene bromide, vinylidene fluoride and vinylidene iodide other comonomers being added if needed in order to improve the compatibility and copolymerization characteristics of the mixed monomers.

Other compounds such as acrylonitrile, and other compounds, e.g., the various substituted acrylonitriles (e.g., methacrylonitrile, ethacrylonitrile, phenylacrylonitrile, etc.), the acrylates and methacrylates including methyl, ethyl, butyl, octyl, etc. acrylate and methacrylate. Other monomers copolymerizable with the instant novel monomers are given, for example, in U.S. Pat. No. 2,601,572, dated June 24, 1952, where examples are given both by classes and species.

Of course, it is also possible to prepare copolymers produced from two or more of the monomers represented by Formula I, above.

Homopolymers of the Formula I compounds where $m=0$ may be prepared by heating at a temperature ranging from about 20° C. to about 150° C., in the absence of a salt or acid, the corresponding vinyl monomer. Suitable catalysts such as those mentioned above may be used. The copolymers of these $m=0$ compounds may be prepared in the same manner.

Homopolymer salts i.e. where $m=1$, may be prepared via a plurality of mechanisms. The particular method employed is not critical except if it is desired to prepare the homopolymer salt from the isolated monomer salt. In such a case, the vinyl monomer where $m=0$ is merely contacted with an acid solution or salt solution to form the corresponding vinyl salt which may then be isolated and polymerized. Homopolymer salts may also be prepared by heating salts of the compounds represented by Formula II at temperatures ranging from 20°-150° C. alone or in the presence of a catalyst, e.g. sulfite-bromate-persulfate mixtures, as is known in the art. The homopolymer salts may also be prepared by heating the Formula II compounds in the presence of an acid or salt or by treating the corresponding homopolymer of the $m=0$ compound with such an acid or salt. Copolymers of the vinyl salts can be prepared by copolymerization of the vinyl salt with the above-disclosed comonomers under the conditions set forth or by contacting the $m=0$ copolymer with a salt or acid in the same manner as with the homopolymers.

It is therefore apparent that if homopolymers and copolymers of the vinyl monomer where $m=0$ are to be prepared, it is essential that the monomeric salts or salts per se be avoided in that they tend to immediately polymerize the vinyl monomers at high temperatures into polymer salts. However, if isolation of the vinyl monomer where $m=0$ is not desired, the salt of the charge materials represented by Formula II above may be heated to the above specified cracking temperature in the absence of a catalyst. In this manner, the hydroxy, alkoxy, aryloxy or alkaryloxy group is cracked, as described above, and the resultant vinyl compound is then immediately polymerized to the homopolymeric salt.

Homopolymeric salts and copolymeric salts, of course, may be converted into non-salts by neutralization and dialysis as is known in the art.

The specific homopolymer of 2-vinyl-2-imidazoline produced by homopolymerizing the monomer where $m=0$ per se, i.e. that polymer having the formula

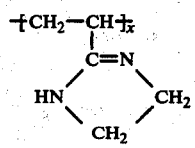
(III)

wherein $x$ is the number of recurring units in the polymer, is distinct from those homopolymers of vinylimidazoline known in the art and produced by reacting polyacrylonitrile with ethylene diamine since the homopolymer of the instant invention is colorless and is free of ester, carboxyl and amide groups, unreacted nitrile groups and also unreacted polyamine.

Additionally, the copolymers of the instant invention wherein the vinyl imidazoline or vinyl amidine is copolymerized with acrylamide are equally exceptional in that no such copolymers were even thought possible heretofore since acrylamide-acrylonitrile copolymers do not enable reaction of the nitrile component with a diamine, according to art recognized methods of production, to the exclusion of the acrylamide component.

The novel homopolymers and copolymers of the instant invention find use as water-treatment additives, i.e. flocculation aids and the like and generally may be used to facilitate the dewatering of aqueous suspensions of organic and/or inorganic materials, as mentioned above. They additionally may be used for lowering the cholesterol levels in warm-blooded animals by administering them to said animals in pharmacologically acceptable amounts.

The homopolymers and homopolymer salts of the instant invention have the structure

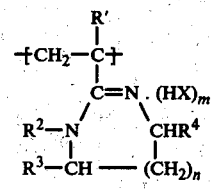

wherein all substituents are as set forth above.
Similarly, the copolymers have the structure

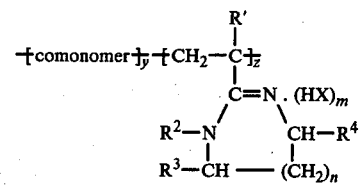

the comonomer being any of those mentioned above and the ratio of $y:z$ being 4:96 to 96:4, as indicated above. The preferred copolymer exists when the comonomer is an acrylamide moiety i.e.

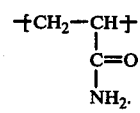

The following examples are set forth for purposes of illustration only and are not to be construed as limitations on the present invention except as set forth in the appended claims. All parts and percentages are by weight unless otherwise specified.

Apparatus and Analytical Methods

The cracking apparatus employed consists of a glass tube fitted with glass joints at top and bottom. The column packing consists of a lower section (10%) of neutral glass beads, 50% of catalyst and neutral glass beads (40%) at the top. The upper section of glass beads acts as a vaporizer for feed. The column is heated either by a furnace or by a larger diameter glass column which is wrapped with nichrome heating wire. Temperature measurements are made with a Leeds and Northrup potentiometer equipped with iron constantan thermocouples. Liquid feed is charged dropwise into the column from a heated addition funnel which has a pressure equilizing side arm and which is equipped with a glass capillary tube through which nitrogen can be fed. Product from the cracker is collected in a round-bottomed vessel attached directly to the bottom of the catalyst column by means of the lower joint. This receiver is cooled in a cooling bath while product is collected. Pressure is controlled by means of a vacuum pump connected to the receiver and with a manometer equipped with a pressure regulator. Condensates are analyzed by NMR and IR.

EXAMPLE 1

To the above-described apparatus, by way of the heated addition funnel, are added dropwise, 100.0 parts of 2-(2-methoxyethyl)-2-imidazoline. The column is packed with barium oxide as the catalyst. The temperature of the column is 410°–425° C. while the pressure (mm Hg) is 0.2. After a period of about 4 hours, 50.0 parts of 2-vinyl-2-imidazoline are recovered. The product is a white, crystalline solid containing a small amount of liquid.

The 100 MHz 'H NMR spectrum of a CDCl$_3$ solution (~5%) of the solid shows eight sharp lines characteristic of the 3 hydrogens in the vinyl group. Their frequency differences (in Hertz) from the internal standard tetramethylsilane are 650, 640, 633, 622, 582, 561, 550. These data yield the following approximate chemical shifts ($\delta$) and coupling constants (J) for the hydrogens as labelled in the figure:

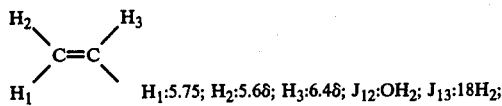

$H_1$:5.75; $H_2$:5.6δ; $H_3$:6.4δ; $J_{12}$:OH$_2$; $J_{13}$:18H$_2$; $J_{23}$:11H$_2$. The NH hydrogen is a broad line at 4.95δ, while the ring —CH$_2$—CH$_2$— hydrogens appear as a single peak at 3.65δ, indicating the equivalence of the two CH$_2$ groups due to rapid exchange of the NH hydrogen. (At lower concentrations, the exchange is slower, and the removal of the CH$_2$ equivalence is seen as a splitting of the 3.65δ peak into two closely spaced triplets).

The areas under each of the peaks correspond to the correct numbers of hydrogens.

EXAMPLES 2–19

Following the procedure of Example 1, various catalysts, pressures and temperature ranges are employed in the cracking of 2-(2-methoxyethyl)-2-imidazoline to 2-vinyl-2-imidazoline. The variables and results are set forth in Table I, below. In the table, C means comparative. In Examples 11–14 and 19, the 2-(2-methoxyethyl)-2-imidazoline charge contains 8.8%, 0%, 27.4%, 51.8% and 2.0% water, respectively.

TABLE I

| Ex. | Catalyst | Temp. °C. | Pressure mmHg | Product Yield |
|---|---|---|---|---|
|  | Alumina Extrudate | 290–306 | 0.2 | 5.0% |
| 3 | Alumina Granules | 266–275 | 0.2 | 5.0% |
| 4 | 1% Barium Oxide on Alumina | 265–274 | 15.0 | 25.0% |
| 5 | Silica Gel | 363–384 | 15.0 | 83.0% |
| 6 | 24% Thorium Oxide on Silica Gel | 340–380 | 15.0 | 40.0% |
| 7 | 24% Calcium Oxide on Silica Gel | 343–388 | 15.0 | 20.0% |
| 8 | 3.8% Barium Oxide on Silica Gel | 340–374 | 15.0 | 63.6% |
| 9 (C) | Glass Helices | 418–425 | 0.1 | 0.0% |
| 10 (C) | Calcium Carbonate Chips | 340–374 | 15.0 | 0.0% |
| 11 | Barium Oxide | 330–340 | 15.0 | 26.5% |
| 12 | " | 329–324 | 0.2 | 13.8% |
| 13 | " | 326–330 | 15.0 | 2.0% |
| 14 (C) | " | 334–338 | 15.0 | 0.0% |
| 15 (C) | " | 269–278 | 0.2 | 0.0% |
| 16 | " | 329–334 | 0.3 | 15.0% |
| 17 | " | 358–369 | 0.2 | 17.0% |
| 18 | " | 427–431 | 0.1 | 43.0% |
| 19 | " | 330–340 | 15.0 | 21.0% |

EXAMPLES 20–32

Again following the procedure of Example 1 except that various alternative charge materials are fed dropwise into the column containing the cracking catalyst, a series of vinyl imidazolines and amidines are produced. In each instance, the yield of desired product is quantitative. The charge variables are set forth in Table II, below.

TABLE II

| | Charge | | | | | | |
|---|---|---|---|---|---|---|---|
| Example | R | R' | R$^2$ | R$^3$ | R$^4$ | n | Product |
| 20 | CH$_3$ | H | CH$_3$ | H | H | 0 | 1-methyl-2-vinyl-2-imidazoline |
| 21 | CH$_3$ | H | C$_7$H$_6$ | H | H | 0 | 1-benzyl-2-vinyl-2-imidazoline |
| 22 | CH$_3$ | C$_6$H$_6$ | H | H | CH$_3$ | 0 | 4(or 5)-methyl-2-(1-phenylvinyl)-2-imidazoline |
| 23 | CH$_3$ | H | CH$_3$ | CH$_3$ | CH$_3$ | 1 | 1,4,5,6-tetrahydro-1,4,6-trimethyl-2-vinylpyrimidine |
| 24 | C$_2$H$_5$ | CH$_3$ | H | CH$_3$ | H | 1 | 1,4,5,6-tetrahydro-2-isopropenyl-6-methylvinylpyrimidine |
| 25 | CH$_3$ | CH$_3$ | C$_4$H$_9$ | H | H | 0 | 1-butyl-2-isopropenyl-2-imidazoline |
| 26 | C$_4$H$_9$ | H | H | H | CH$_3$ | 0 | 4(or 5)-methyl-2-vinyl-2-imidazoline |
| 27 | CH$_3$ | H | C$_6$H$_5$ | H | H | 0 | 1-phenyl-2-vinyl-2-imidazoline |
| 28 | C H | CH$_3$ | H | H | C$_2$H$_5$ | 1 | 4-ethyl-1,4,5,6-tetrahydro-2-isopropenylpyrimidine |
| 29 | C$_{10}$H$_7$ | H | H | H | H | 0 | 2-vinyl-2-imidazoline |
| 30 | C$_{10}$H$_{21}$ | H | H | C$_7$H$_7$ | H | 0 | 4(or 5)-tolyl-2-vinyl-2-imidazoline |
| 31 | C$_7$H$_7$ | H | C$_{10}$H$_7$ | H | H | 0 | 1-naphthyl-2-vinyl-2-imidazoline |
| 32 | CH$_3$ | H | H | C$_{11}$H$_9$ | H | 0 | 4(or 5)-(naphthylmethyl)-2-vinyl-2-imidazoline |

EXAMPLE 33

The procedure of Example 1 is again followed except that the 2-vinyl-2-imidazoline product is allowed to collect in a round-bottomed vessel containing sulfuric acid. A stable, white, crystalline solid is then recovered and shown to be 2-vinyl-2-imidazoline sulfate. A solution of this 2-vinyl-2-imidazoline sulfate salt (14.0 weight percent) is charged to a suitable polymerization vessel equipped with a stirrer and means for deaeration. After adjusting the pH to 3.0 with 50% aqueous sodium hydroxide solution and then deaerating with a stream of nitrogen for 2 hours, polymerization is initiated by adding 16.7 ppm (based on imidazoline salt) of sodium sulfite followed by 263 ppm each (based on imidazoline salt) of sodium bromate and ammonium persulfate. After polymerizing 2 days at room temperature, the syrupy polymer solution is concentrated by evaporation under vacuum to a more viscous syrup from which the polymer is precipitated by pouring into an excess of ethanol in a Waring blendor. After filtration followed by drying in vacuo over calcium chloride, the polymer consists of light yellow-colored granules. The polymer is redissolved in water, reprecipitated into ethanol, filtered and dried in vacuo. This treatment produces a white polymer with an intrinsic viscosity of 1.30 dl/gm in 1N NaCl solution. NMR and IR analysis of the polymer show that it is the sulfate salt of poly(2-vinyl-2-imidazoline) uncontaminated by nitrile, diamine, ester or amide groups. It should be noted that the structure of our polymer, i.e.,

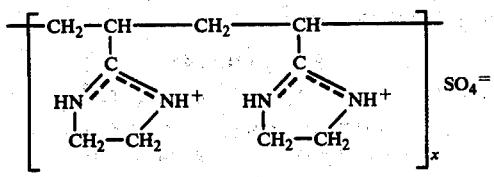

is different from that of the art, see especially U.S. Pat. No. 3,450,646, which claims the following structure

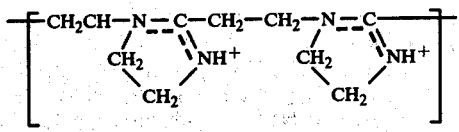

Both NMR and IR spectra show that the above structure is absent from the instant homopolymer.

The polymer effectively clarifies raw water.

EXAMPLE 33A

Into a suitable distillation vessel equipped with a condenser and dry ice-cooled receiver are weighed 3.0 parts of 2-(2-methoxyethyl)-2-imidazoline hydrochloride (M.P. 102.5°–104° C.). A pre-heated oil bath at a temperature of 183° C. is used to heat the distillation vessel for 35 minutes, during which time the contents bubble and become viscous and condensate collects in the receiver. This condensate is identified as a 75/25 methanol/water solution by IR. The yellowish-colored resin remaining in the vessel is completely water-soluble and is identified as poly(2-vinyl-2-imidazoline) hydrochloride:

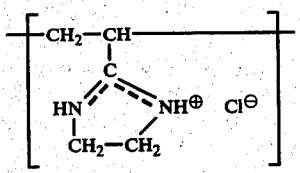

contaminated with a small amount of starting material. This polymer is an effective clarification aid for raw water.

The polymers of Examples 33 and 33A are 100% poly (2-vinyl-2-imidazoline) salts, uncontaminated by nitrile, amide or ester groups or by ethylenediamine salts, or yet further by imino or ketonic groups along the carbon backbone of the polymer. In this regard, they are different from the poly 2-vinyl-2-imidazoline salts disclosed in U.S. Pat. No. 3,406,139, where the imidazoline or pyrimidine salt polymers are prepared from preformed polyacrylonitrile. It has been recently demonstrated that polyacrylonitrile manufactured by free radical polymerization techniques contains imino (=NH) and/or ketonic groups along the polymer backbone, see On The Chromophore of Polyacrylonitrile III, The Mechanism of Ketone Formation in Polyacrylonitrile, J. Brandrup, J. R. Kirby and L. Peebles, Jr.; Macromolecules 1, 59–63, (1968); Side Reaction in Acrylonitrile Radical Polymerization, L. Patron and M. Bastianelli, Paper presented at the A.C.S. Special Symposium on Acrylonitrile in Macromolecules, 166th A.C.S. National Meeting, Chicago, Illinois, Aug. 27–29, 1973.

These defects along the backbone of the polyacrylonitrile carbon-carbon backbone are postulated to arise from occasional so-called abnormal reactions:

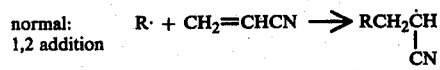
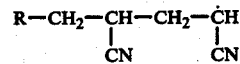
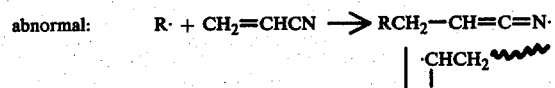
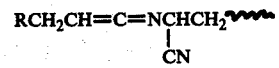
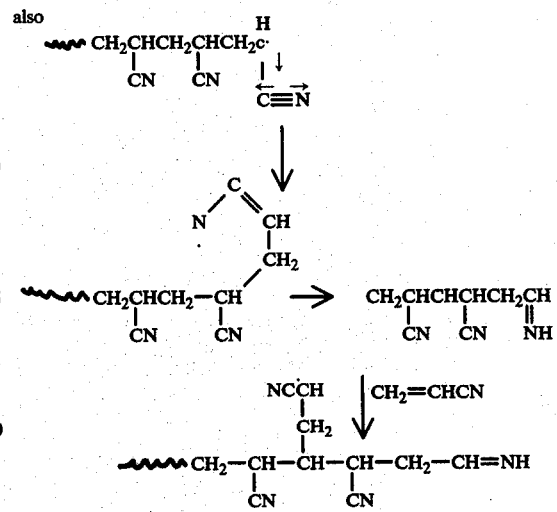

Since polyacrylonitrile itself is not 100% pure (some of the nitrile groups having taken part in "abnormal" reactions during polymer synthesis) and since very few chemical transformations go to 100% conversion, the polyvinylimidazoline salts of the prior art cannot be 100% pure poly 2-vinyl-2-imidazoline salts as are the polymers of the instant examples.

EXAMPLES 34–46

The monomers of Examples 20–32 are individually contacted with aqueous acid solutions in order to convert them to their corresponding salts as set forth in Example 33 except that the salts are isolated and recovered rather than homopolymerized. The compounds produced are:

(34) 1-methyl-2-vinyl-2-imidazoline nitrate;
(35) 1-benzyl-2-vinyl-2-imidazoline acetate;
(36) 4 (or 5)-methyl-2-(1-phenylvinyl)-2-imidazoline sulfate;
(37) 1,4,5,6-tetrahydro-1,4,6-trimethyl-2-vinylpyrimidine nitrate;
(38) 1,4,5,6-tetrahydro-2-isopropenyl-6-methylvinylpyrimidine sulfate;
(39) 1-butyl-2-isopropenyl-2-imidazoline citrate;

(40) 4 (or 5)-methyl-2-vinyl-2-imidazoline tartrate;
(41) 1-phenyl-2-vinyl-2-imidazoline acetate;
(42) 4-ethyl-1,4,5,6-tetrahydro-2-isopropenylpyrimidine malonate;
(43) 2-vinyl-2-imidazoline benzoate (10% solution of benzoic acid in dimethyl formamide used);
(44) 4 (or 5)-tolyl-2-vinyl-2-imidazoline nitrate;
(45) 1-naphthyl-2-vinyl-2-imidazoline citrate;
(46) 4 (or 5)-(naphthylmethyl)-2-vinyl-2-imidazoline tartrate.

EXAMPLE 47

A solution of 17.0 parts 2-vinyl-2-imidazoline, 43.0 parts of styrene and 140.0 parts of toluene is prepared in a suitable polymerization vessel equipped with means for stirring and deaeration and temperature controls. After deaeration for 1 hour with a stream of nitrogen, the temperature is raised to 60° C. and polymerization is initiated by the addition of 100 ppm (based on total weight of imidazoline) of azobisisobutyronitrile as a 1.0% solution in methanol. After allowing the polymerization to proceed overnight at a temperature of 60°–70° C., the polymer is precipitated from the resulting viscous solution by pouring it into an excess of methanol with vigorous stirring. The resultant yellowish colored polymer is redissolved in toluene and then re-precipitated once more by pouring into methanol. IR and NMR analysis of dried polymer show about 75 mole percent styrene and 25 mole percent 2-vinyl-2-imidazoline incorporated into the copolymer. A sample of the polymer is an effective sizing agent for 50/50 Albacel-Astracel pulp (bleached hardwood-softwood Kraft pulp).

EXAMPLE 48

A solution of 14.7 parts of 2-methoxyethylimidazoline and 0.15 part of distilled water are fed to the cracking apparatus described above at 381°–386° C. and at 16 mm Hg pressure. Effluent from the cracking operation is collected in a flask which contains 109.2 parts of 10.32% sulfuric acid which has been cooled in ice water. The resultant solution of 2-vinyl-2-imidazoline sulfate is extracted once (40 minutes at room temperature) with 2.0 parts of activated carbon which had previously been treated with dilute sulfuric acid followed by 0.1% copper sulfate solution (7:1 weight ratio of copper sulfate solution to activated carbon) so as to render the activated carbon inactive as a cause of polymerization. The resultant solution after filtration has a pH of 0.8, a slight greenish-yellow color and analyzes 4.23% 2-vinyl-2-imidazoline (as the free base) by NMR.

To 80.2 parts of the 2-vinylimidazoline sulfate solution are added 46.9 parts of dry acrylamide crystal and 227.9 parts of deionized water. After solution is complete, the pH is 1.50. 5.03 Parts of 50% sodium hydroxide solution are added so as to raise the pH to 3.00. The resultant solution is deaerated with a stream of nitrogen in a suitable polymerization vessel and polymerization is initiated by aqueous solutions of sodium sulfite, ammonium persulfate and sodium bromate (8 ppm of sodium sulfite and 155 ppm each of persulfate and bromate, based on imidazoline salt charged). After 15 hours, a tough rubbery gel is obtained. A portion of this gel is extracted with methanol, dried in vacuo and milled. A solution (0.10% in 1N NaCl) of the resultant white powder has a viscosity of 2.63 cps. when measured with a Brookfield LVT viscometer with UL adapter at 60 rpm and 25° C. By IR analysis, the copolymer contains 5–10% of 2-vinylimidazoline sulfate while NMR analysis substantiates this result. The copolymer effectively clarifies brackish water.

EXAMPLE 49

The copolymer of Example 48 is added (0.11% on dry sludge solids) to New Rochelle mixed primary digester sludge and proves to be an effective dewatering aid. Homopolymeric acrylamide is ineffective when used alone on this sludge.

EXAMPLE 50

Following the procedure of Example 1, 16.46 parts of feed consisting of 6.5% water and 93.5% of 2-(2-methoxymethyl)-2-imidazoline, is cracked over a regenerated silica gel at 364°–384° C. and a pressure of 13–15 mm Hg. The brown, semicrystalline condensate which results is analyzed by NMR which indicates an 85% conversion to 2-vinylimidazoline at a selectivity of 98%.

The condensate is dissolved in 250 parts of anhydrous diethyl ether and the solution is poured into a solution of 30.0 parts of 15.75% (W/W) anhydrous hydrochloric acid in anhydrous diethyl ether and 70 parts of anhydrous diethyl ether. A crystalline precipitate forms immediately. The precipitate, 2-vinyl-2-imidazoline hydrochloride is filtered through a fritted glass funnel and the crystals are washed several times with fresh diethyl ether.

A solution of 3.55 parts of dry acrylamide crystal in 30 parts of deionized water is prepared in a suitable reaction vessel equipped with stirrer, thermometer, addition funnel, nitrogen inlet and outlet and cooling bath. A solution of 6.6 parts of the 2-vinyl-2-imidazoline hydrochloride in 20 parts of deionized water is placed in the addition funnel. The two solutions are deaerated with nitrogen and the temperature is adjusted to 31° C. Polymerization of the acrylamide in the vessel is initiated by the addition of 6.2 ppm of sodium sulfite and 79 ppm each of ammonium persulfate and sodium bromate (based on charged monomer). Cooling is initiated and the 2-vinyl-2-imidazoline hydrochloride solution is added incrementally over 50 minutes while the vessel is maintained at 30.5°–32° C. After all the monomer salt is added, an additional charge of catalyst equal to the first is charged and the copolymerization is allowed to proceed overnight. After precipitation of the resultant copolymer in methanolether, washing, filtering and drying, IR analysis shows a copolymer of 50% acrylamide-50% 2-vinyl-2-imidazoline hydrochloride.

EXAMPLE 51

Use of the copolymer of Example 50 as a dewatering aid on New Rochelle sludge shows excellent results.

EXAMPLE 52

A solution of 10.0 parts acrylamide, 0.12 part of a commercially available anionic emulsifier and 41.7 parts of deionized water is prepared in a suitable polymerization vessel equipped with means for stirring, monomer addition, deaeration and temperature control. After the acrylamide and anionic emulsifier have dissolved, a solution of 2.25 parts of 2-vinyl-2-imidazoline sulfate at pH 3.5 is added. After deaeration for 30 minutes at room temperature, 1.83 parts of styrene are added, then the solution is heated to 75° C., when 0.19% (based on total weight of monomers) as a 2.0% aqueous deaerated solution is added. The temperature is controlled at 74°–85°

C. for 4½ hours and then allowed to cool down to room temperature overnight. The reaction mixture is a turbid viscous solution. A sample of the polymer solution is tested as a dry strength agent for tissue paper and is found to be effective. Another sample of the terpolymer is an effective drainage aid for unbleached Kraft linerboard stock with 3% black liquor, 1% alum and at pH 5.5.

EXAMPLE 53

A solution of 1.16 parts of 1,2-dimethyl-2-imidazoline in 7.0 parts of benzene is prepared in a round-bottomed distillation flask and then 0.47 part of paraformaldehyde and 0.05 part of phenothiazine are added. After connecting the flask to an 8 inch, glass-helices-packed column equipped with a reflux head, the mixture is heated to reflux for half an hour during which time a solution is obtained. After standing and cooling overnight, the solution is reheated to reflux for half an hour, by which time the theoretical amount of water of reaction has been recovered. IR analysis of the reaction mixture indicates almost 100% conversion of starting material to mainly 2-(2-hydroxyethyl)-3-methyl-2-imidazoline.

The benzene is stripped from the reaction mixture and then the high boiling residue is heated to 170°-194° C. overnight during which time water distills out. No 2-vinyl-3-methyl-2-imidazoline is recovered. A hard brittle resin remains in the distillation flask. This resin is dissolved in isopropyl alcohol and precipitated in diethylether twice and then dried in vacuo overnight. IR analysis of the polymer shows it to be poly(2-vinyl-3-methyl-2-imidazoline).

The polymer is shown to be an excellent dewatering aid when used to treat organic waste contaminated water.

EXAMPLE 54

Following the procedure similar to that of Example 48, a solution of 225 parts of 2-vinyl-2-imidazoline sulfate, 56 parts acrylamide and 168 parts of deionized water, after adjusting the pH to 3.0, is placed in a suitable polymerization vessel and deaerated with a stream of nitrogen for 2 hours. Polymerization is initiated at room temperature by adding 14.0 ppm of sodium sulfite and 280 ppm each of sodium bromate and ammonium persulfate (based on total weight of monomers charged). After polymerization is complete (overnight) a tough rubbery gel, from which the polymer is isolated by the same procedure as in Example 48, is obtained. The viscosity of a 0.10% solution of the dried polymer in 1N NaCl at 25° C. using a Brookfield LVT viscometer with UL adapter at 60 rpm is 2.56 cps. Both NMR and IR analyses confirm that the polymer contains 5-10 mole percent poly 2-vinyl-2-imidazoline sulfate (NMR gives about 7.5 mole percent and IR 5-10 mole percent).

A sample of this polymer is tested as a drainage and retention aid for Eucalyptus pulp and gives the results in Table III, below. This pulp has a Canadian Standard Freeness (CSF) of 310 ml and the conditions are: 10% clay, 1% rosin size, 2% alum and pH 4.8.

TABLE III

The Effectiveness of 92.5/7.5 Acrylamide/2-Vinyl-2-Imidazoline Sulfate Copolymer as a Drainage and Retention Aid

| Polymer Added-% on Dry Fiber | Drainage-Time Secs. | Clay Retained-%[1] |
|---|---|---|
| 0 | 44.4 | 7.64 |
| 0.02 | 32.6 | 8.14 |
| 0.04 | 29.0 | 8.14 |
| 0.06 | 28.2 | 8.20 |
| 0.08 | 28.0 | 8.20 |
| 0.10 | 30.3 | 8.19 |

[1]Determined by ashing samples of dried treated pulp.

Another sample of the same polymer is tested as a drainage aid for "old news", recovered newspaper pulp, at pH 7 and gives the results listed in Table IV, below.

TABLE IV

The Effectiveness of a 92.5/7.5 Acrylamide/2-Vinyl-2-Imidazoline Sulfate Copolymer as a Drainage Aid Conditions: "Old News" pH 7.0.
A blank took 51 secs. to drain.

| Polymer Added-% of Dry Fiber | Improvement in Drainage-Seconds |
|---|---|
| 0.05 | 21 |
| 0.10 | 28 |
| 0.15 | 34 |
| 0.20 | 37 |
| 0.25 | 40 |
| 0.30 | 41 |

A third sample of the same polymer is tested as a drainage aid for "old news" with 2% alum, 1% rosin size and pH 4.5 and gives the results listed in Table V, below.

TABLE V

The Effectiveness of a 92.5/7.5 Acrylamide/2-Vinyl-2-Imidazoline Sulfate Copolymer as a Drainage Aid Conditions: 2.0% alum, 1.0% resin size, pH 4.5
A blank took 37 secs. to drain

| Polymer Added-% on Dry Fiber | Improvement in Drainage-Seconds |
|---|---|
| 0.05 | 20 |
| 0.10 | 23 |
| 0.15 | 24 |
| 0.20 | 24 |
| 0.25 | 12 |

Polyacrylamide containing no cationic comonomer is ineffective as a drainage aid; the drainage time actually increases.

EXAMPLE 55

To a solution of 26.0 parts of a commercially available mineral oil solvent and 2.6 parts of a commercially available fatty acid sorbitan surfactant is added a solution fo 24.4 parts of acrylamide in 24.4 parts of deionized water and 18.1 parts of 2-vinyl-2-imidazoline sulfate solution prepared and purified as in Example 48. Before adding the aqueous solution to the hydrocarbon solution, the pH is adjusted to 3.5 and 30 ppm of ethylenediamine tetraacetic acid (based on total monomer) are added. The two solutions are placed in a suitable polymerization vessel and stirred vigorously so as to obtain a smooth emulsion. After reducing the stirring speed, 100 ppm of sodium bromate (based on total monomer) are added as a 0.87% aqueous solution and then the emulsion is deaerated with a stream of nitrogen for 1.2 hours at room temperature. During the next 6.7 hours, 120 ppm sodium bisulfite, as an 0.205% aqueous solution, are fed in and the temperature is allowed to increase to 40° C. at which point cooling is started and maintained for about 40 minutes. Thereafter, for the remainder of the 6.7 hours, the polymerization proceeds without cooling. A smooth, coagulum-free, polymer emulsion is obtained and the conversion of monomer to polymer is 97.7%. The viscosity of a 0.10% (real polymer basis) solution in 1N NaCl at 25° C. using a Brookfield viscometer with UL adapter at 60 rpm is 2.6 cps. The molar composition of this polymer is 95/5 acrylamide/2-vinyl-2-imidazoline sulfate.

EXAMPLE 56

Following the procedure of Example 55, a 90/10 acrylamide/2-vinyl-2-imidazoline sulfate copolymer emulsion is prepared, but in this case a small amount of coagulum is formed. The viscosity of a 0.10% solution (dry polymer salt basis) in 1N NaCl at 25° C. using Brookfield LVT viscometer with UL adapter at 60 rpm is 2.2 cps and the conversion of monomer to polymer is 97.8%.

Samples of the polymers from Examples 54, 55 and 56 are tested on sewage sludge dewatering agents on Greenwich, Connecticut mixed primary waste activated sludge containing 2.5% solids. The results of the tests are presented in Table VI, below. Polyacrylamide containing no cationic comonomer residues is ineffective in dewatering this sludge. The test is a standard Buchner funnel filtration test utilizing 150 ml of sludge mixed with 30 ml of a solution of the polymer to be tested for each dosage level.

TABLE VI

Evaluation of Various Polymers As Sewage Sludge Dewatering Agents
Greenwich, Conn. mixed primary waste activated sludge (2.5% solids)

| Dosage, lb. Polymer/Ton Sludge Solids | MI Filtrate Collected in 1 Minute | | |
|---|---|---|---|
| | Polymer From Example 54 | Polymer From Example 55 | Polymer From Example 56 |
| 0 | 14 | 14 | 14 |
| 3.21 | 38 | 22 | 20 |
| 6.42 | 60 | 29 | — |
| 9.63 | 65 | — | 24 |
| 12.8 | 115 | 43 | — |
| 19.3 | 130 | — | 28 |
| 25.7 | 106 | 74 | — |
| 48.2 | — | 132 | 78 |

EXAMPLE 57

The 1-methyl-2-vinyl-2-imidazoline of Example 20 (100 parts) is fed into a suitable reaction vessel equipped with a stirrer and deaeration means. The vessel is deaerated as in Example 33 and 92.0 ppm of azobisisobutyronitrile and 150 parts of toluene are added. The polymerization reaction is allowed to proceed for 36 hours at 57° C. after which time the polymer is recovered by precipitation from methanol. Analysis shows a homopolymer of 1-methyl-2-vinyl-2-imidazoline free of nitrile, amide or ester groups. No imino or ketonic groups are detected in the polymer backbone. The homopolymer effectively aids in dewatering high solids sludge.

EXAMPLES 58-67

Following the procedure of Example 57, the vinyl imidazolines or unsaturated pyrimidines of Examples 21-32 are homopolymerized into polymers. The homopolymers are all free of nitrile, amide or ester groups. Each product exhibits the ability to assist in dewatering organic waste sludge.

EXAMPLES 68-77

The monomers of Examples 21-32 are copolymerized with styrene according to the procedure of Example 47. Similar results are attained. The resultant copolymers exhibit the usefulness shown for the polymer of Example 47.

EXAMPLES 78-90

Following the procedure of Example 52, the monomers of Examples 34-46 are copolymerized with acrylamide. The resultant copolymers are shown to be effective dry strength agents and drainage aids.

EXAMPLES 91-103

Following the process set forth in Example 33A, the monomers of Examples 34-46 are homopolymerized into polymers uncontaminated by nitrile, amide or ester groups or ethylenediamine salts or imino and ketonic groups. They are effective water clarifiers.

We claim:

1. A method for the production of a compound having the formula

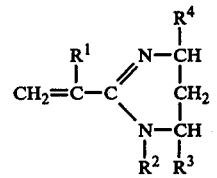

wherein $R^1$ is hydrogen, methyl or phenyl and $R^2$, $R^3$ and $R^4$ are, individually, hydrogen, alkyl ($C_1$-$C_4$), aryl ($C_6$-$C_{10}$), aralkyl ($C_7$-$C_{11}$) or alkaryl ($C_7$-$C_{11}$) which comprises heating, to a temperature ranging from about 275° C., to about 500° C., a starting compound having the formula

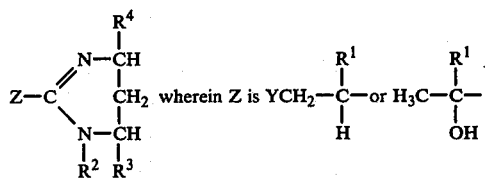

Y being hydroxyl or RO, wherein R is alkyl ($C_1$-$C_{10}$), aryl ($C_6$-$C_{10}$) or aralkyl ($C_7$-$C_{11}$) and $R^1$, $R^2$, $R^3$ and $R^4$ are as described above, in the presence of a heterogeneous vapor phase catalyst and up to about 30%, by weight, based on the weight of said starting compound, of water and recovering the resultant compound.

2. A method according to claim 1, wherein said catalyst is barium oxide.

3. A method according to claim 1 wherein said catalyst is silica gel.

4. A method according to claim 1 wherein said catalyst is barium oxide on silica gel.

5. A method according to claim 1 wherein from about 2.0% to about 30% water is present.

6. A method according to claim 1 wherein said catalyst is barium oxide and from about 2.0% to about 30% water is present.

7. A method for the production of a compound having the formula wherein X is an anion, R' is hydrogen, methyl or phenyl and $R^2$, $R^3$ and $R^4$ are, individually, hydrogen, alkyl ($C_1$-$C_4$), aryl ($C_6$-$C_{10}$), aralkyl ($C_7$-$C_{11}$) or alkaryl ($C_7$-$C_{11}$) which comprises heating to a temperature ranging from about 275° C. to about 500° C., a starting compound having the formula

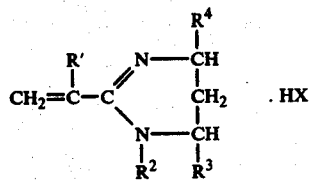

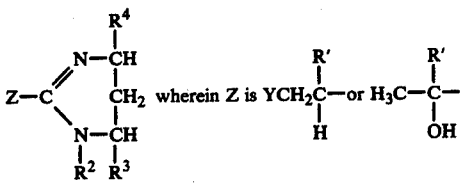

Y being hydroxyl or RO, wherein R is alkyl ($C_1$-$C_{10}$), aryl ($C_6$-$C_{10}$) or aralkyl ($C_7$-$C_{11}$) and $R^1$, $R^2$, $R^3$ and $R^4$ are as described above, in the presence of a heterogeneous vapor phase catalyst and up to 30%, by weight, based on the weight of said starting compound, of water, contacting the compound so produced with an acid in the liquid state and recovering the resultant compound.

8. A method according to claim 7 wherein said catalyst is barium oxide.

9. A method according to claim 7 wherein said catalyst is silica gel.

10. A method according to claim 7 wherein said catalyst is barium oxide on silica gel.

11. A method according to claim 7 wherein from about 2.0% to about 30% water is present.

12. A method according to claim 7 wherein said catalyst is barium oxide and from about 2.0% to about 30% water is present.

* * * * *